United States Patent [19]

Sugawara et al.

[11] 4,402,211
[45] Sep. 6, 1983

[54] SYSTEM FOR MONITORING ABNORMALITY OF OIL-FILLED ELECTRIC DEVICES

[75] Inventors: Katuo Sugawara; Etsuo Ohe, both of Hitachi; Ichitaro Tani, Kitaibaraki; Hideo Tsukioka, Mito, all of Japan

[73] Assignee: Hitachi, Ltd., Tokyo, Japan

[21] Appl. No.: 265,656

[22] Filed: May 20, 1981

[30] Foreign Application Priority Data

May 20, 1980 [JP] Japan .................................. 55-65903
Jun. 5, 1980 [JP] Japan .................................. 55-74973

[51] Int. Cl.³ .............................................. G01N 7/10
[52] U.S. Cl. ........................................ 73/19; 73/23.1; 73/863.23
[58] Field of Search ................................. 73/19, 23.1

[56] References Cited

U.S. PATENT DOCUMENTS

| | | | |
|---|---|---|---|
| 3,460,909 | 8/1969 | Gayle | 422/89 |
| 3,772,909 | 11/1973 | Anderson | 73/23.1 |
| 4,058,373 | 11/1977 | Kurz . | |
| 4,112,737 | 9/1978 | Morgan . | |
| 4,251,870 | 2/1981 | Jaffe | 73/23.1 |

*Primary Examiner*—S. Clement Swisher
*Attorney, Agent, or Firm*—Antonelli, Terry & Wands

[57] ABSTRACT

A system for monitoring an abnormality of an oil-filled electric device by detecting the components of the gas dissolved in the insulating oil. A gas-in-oil separator which separates the gas from the insulating oil, a gas reservoir where the separated gas is collected, an air feeder which supplies air for delivering out the gas in said gas reservoir, a separating column packed with a gas separating filler whereby the gas supplied from the gas reservoir is separated into the components, a combustible gas detector element disposed in a case which connects at its one end to the outlet of said separating column, and a change-over valve disposed at a location connecting said gas reservoir, are provided. The air feeder and said separating column are adapted to switch a route passing the air from the air feeder into the separating column along with the gas via the gas reservoir to or from a route passing the air directly into the separating column. This system is capable of easily detecting the components in the gas in the insulating oil to allow monitoring of an abnormality with high reliability. Also, according to the system of this invention, at least the components $CH_4$ and $H_2$ in the separated gas are measured separately, and in case it is judged that an abnormality is present, the type of such abnormality is judged from the ratio of said components.

12 Claims, 11 Drawing Figures

SYSTEM FOR MONITORING ABNORMALITY OF OIL-FILLED ELECTRIC DEVICES

BACKGROUND OF THE INVENTION

1. Field of the Invention

This invention relates to a system for monitoring an abnormality of oil-filled electric devices such as transformer, reactor, etc., and more particularly it relates to a system for monitoring abnormality in an oil-filled electric device by separating and extracting the gas produced and dissolved in the insulating oil in said device in the event of occurrence of any electrical or thermal abnormality in the case of said device.

2. Description of the Prior Art

It is well known that when an abnormality such as local overheating or partial discharging occurs in a oil-filled electric device such as transformer, rectifier, capacitor, cable, etc., the insulating oil or solid insulated article is decomposed to produce the hydrocarbon type gases such as $H_2$, $CH_4$, $C_2H_2$, $C_2H_4$, $C_2H_6$, etc., and/or other types of gas such as $CO$, $CO_2$, etc., and most of these gaseous substances stay dissolved in the insulating oil. Therefore, if the gaseous substances dissolved in the insulating oil in a oil-filled electric device are constantly monitored, it is possible to detect abnormality in said device in its early stage.

According to the conventional monitoring systems of this type, internal abnormality of an oil-filled electric device such as transformer is assumptively judged by detecting the concentrations or increments of the various gas components in the oil. To be more specific, according to such conventional monitoring systems, the gas in the insulating oil is separated and collected by a device such as a gas-in-oil separator utilizing Torricelli's vacuum, Toepler pump, piston reciprocation or a gas separating membrane made of an inorganic or organic material provided in the case of the electric device, and the collected gas is measured by gas chromatography or combustible gas sensors to judge presence or absence of abnormality in the device from the total amount of the gas or the absolute amounts of the individual gas components such as $H_2$, $CO$, $CH_4$, $C_2H_4$, $C_2H_6$, $C_3H_8$, etc., or from the degree of increments thereof.

Among the known means for detecting the gas dissolved in the insulating oil in an oil-filled electric device is a system in which the gas dissolved in the insulating oil is separated from said oil and collected in a gas reservoir and then the concentration of the gas in said reservoir is detected by a gas detector, as for instance disclosed in Japanese Laid-Open Patent Application No. 9718/1979 and U.S. Pat. Nos. 4,058,373 and 4,112,737. Since the gas contained in the insulating oil is mostly combustible gas such as hydrocarbon type gas, a commercially available combustible gas detecting element is adaptable as gas detector.

This system is capable of detecting occurrence of abnormality in an oil-filled device from the concentration of the gas collected in the gas reservoir and is also simple in structure. However, it is difficult with this system to detect the components of the gas. In order to detect the gas components by using this system, it is necessary to install the gas detector elements, each having sensitivity to a specific gas alone, that is, having high-degree gas selectivity, in as many number as the gas components to be detected. This is unrealistic.

If the components of the gas separated from the insulating oil can be detected, it becomes possible to assume the type of the abnormality in the oil-filled device, for example, whether such abnormality is occurrence of discharging, local overheating or decomposition of the solid insulated article, and a quite useful device can be provided.

For detecting the gas components in the insulating oil, a system is known in which the insulating oil is sampled into a vessel, then air is blown into the oil to cause bubbling and the gas extracted thereby from the insulating oil is passed through a separating column to separate the gas into the individual components, and then the concentration of each component is detected by a low-selectivity combustible gas detector.

However, as this system is incapable of bubbling the oil in the oil-filled device, it is required to sample out the insulating oil from the device for detecting the gas components. This is very troublesome and uneconomical. It is to be further noted that this type of gas component detecting systems are required to detect the gas components periodically for a prolonged period of time and to also constantly monitor the gas components. Therefore, it is inexpedient for this system to collect the insulating oil from the oil-filled device for every run of detection.

Further, it has been difficult with these conventional systems to know the type of abnormality and the temperature of abnormal heating automatically and in a simple way.

SUMMARY OF THE INVENTION

An object of this invention is to provide a system for monitoring an abnormality of oil-filled electric devices with high reliability whereby it is possible to easily detect the gas components in the insulating oil in an oil-filled electric device with no need of sampling out the insulating oil from said device.

Another object of this invention is to provide a system for monitoring an abnormality of oil-filled electric devices which system is capable of not only merely detecting abnormality but also automatically and easily letting known the type of abnormality in the event of detection of abnormality, that is, capable of indicating whether such abnormality is occurrence of discharging, heating of the insulating oil alone or heating of the insulating oil including the solid insulated article such as insulated paper, press board, etc.

In order to accomplish these objects, this invention provides a system for detecting the components of the gas staying dissolved in the insulating oil in an oil-filled electric device, said system comprising a gas-in-oil separator which separates said gas from the insulating oil in an oil-filled electric device, a gas reservoir in which the separated gas is collected, an air feeder which supplies air for delivering out the gas from said gas reservoir, a separating column packed with a gas separating filler which separates the components of the gas delivered from said gas reservoir, a gas detector unit comprising a combustible gas detector element disposed in a case which connects at its one end to the outlet of said separating column and opens at its other end into the atmosphere, and a change-over valve for switching a route which passes air from said air feeder into said separating column together with said gas via said gas reservoir to and from a route which passes said air directly into said separating column.

It is also a feature of the system for monitoring an abnormality of oil-filled electric devices according to this invention that the amounts of at least two components, or $CH_4$ and $H_2$, in the separated gas are measured separately to determine the ratio of said components and the type of abnormality is judged from the determined ratio of said components in the event of detection of abnormality.

DETAILED DESCRIPTION OF THE INVENTION

Figure 1:
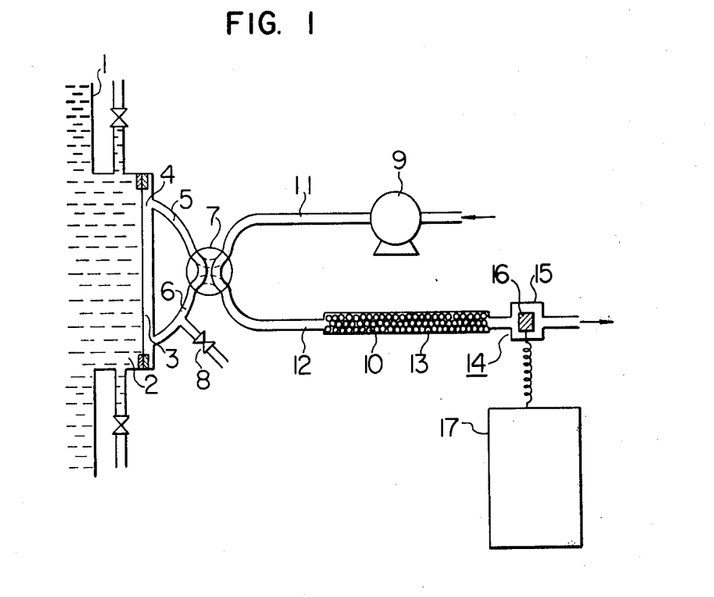
FIGS. 1 to 4 are structural diagrams exemplifying the oil-filled electric devices, incorporating the system of this invention.

The system for monitoring an abnormality of oil-filled electric devices according to this invention is provided in a case 1 which houses the body portion of an oil-filled electric device (not shown) and which is also filled with an insulating oil 2 as shown in FIG. 1. A polymer membrane 3 is provided to an opening formed at a part of said case 1 or to a small chamber provided separately from but in connection to the case 1. This polymer membrane 3 is in contact with the insulating oil 2 and allows passage therethrough of the gas components such as $H_2$, CO, $CH_4$, $C_2H_2$, $C_2H_4$, etc., which stay dissolved in the oil. Outside said polymer membrane 3 is formed a gas reservoir 4 for pooling the gas which has permeated through said membrane 3. This gas reservoir 4 is provided with an inlet side passage 5 and an outlet side passage 6 both of which connect to a four-way change-over valve 7. A gas sampling valve 8 is also provided to the gas reservoir 4.

It will be also seen that an air feeder 9 comprising a compressor, etc., and a gas component separating column 10 are connected to the four-way change-over valve 7 via the passages 11 and 12, respectively. The four-way change-over valve 7 is adapted to switch a route which directly communicates the air feeder 9 and the separating column 10 by closing the gas reservoir 4 as shown by the solid lines in the drawing to and from a route which communicates the air feeder 9, gas reservoir 4 and separating column 10 as shown by the broken lines.

The separating column 10 is packed with a gas separating filler 13 which separates the gas into the respective components while the gas delivered from the gas reservoir 4 passes in said column 10. Active carbon or the like may be used as the filler 13.

A gas detector unit 14 is provided at the outlet of the separating column 10. This gas detector unit 14 comprises a combustible gas detector element 16 disposed in a case 15 which connects at its one end to the outlet of the separating column 10 and opens at its other end into the atmosphere, and the electrical change induced upon contact of said gas with said combustible gas detector element 16 is detected by a detection circuit 17.

As the combustible gas detector 16, there may be used, for example, a semiconductor element which is changed in its internal impedance upon contact with a combustible gas or a so-calld catalytic combustion type gas detector element using a metal which is heated by catalytic combustion heat generated from adsorption of combustible gas-containing air on a catalyst heated to an appropriate temperature, with the resulting change in electrical resistance of the metal being detected by the detector. These combustible gas detector elements retain normal output characteristics in the presence of air, and various types of such elements are commercially available. It is also desirable to use a combustible gas detector element which is capable of detecting various types of combustible gas, in other words, an element which has as small selectively as possible.

The case 15 that houses said separating column 10 and combustible gas detector element 16 is preferably placed in a thermostatic chamber so that, in use, it remains heated to a constant temperature.

In operation of the present system, the four-way change-over valve 7 is first set at its solid-line position in the drawing to keep the gas reservoir 4 closed for a given period of time, allowing the gas dissolved in the insulating oil 2 to permeate through the polymer membrane 3 into the gas reservoir 4. Since an equilibrated relation exists between the pressure of a gas component which has passed through said polymer membrane 3 and the concentration of the same gas component which stays dissolved in the insulating oil, it is possible to know the concentration of such gas component in the insulating oil 2 by detecting the concentration (or pressure) of the same gas component in the gas reservoir 4.

Upon passage of a given period of time, the air feeder is operated, with the four-way change-over valve 7 kept at its solid-line position, to pass air through the separating column 10 and the case 15, thereby creating a perfectly combustible gas-free condition in said both separating column 10 and case 15 to thereby effect zero-point adjustment of the gas detector unit 14. Thereafter, the four-way change-over valve 7 is switched to the position of the broken lines, whereby the gas in the gas reservoir 4 is forced out to flow into the separating column 10 by the air from the air feeder 9. The gas is separated into the respective components while passing in the separating column 10 and the separated gas components are discharged out successively from the outlet of the separating column 10. For example, in case active carbon is used as the gas separating filler 13 and if it is supposed that $H_2$, CO and $CH_4$ are contained in the gas in the gas reservoir 4, then the gas is separated into $H_2$, CO and $CH_4$ in the separating column 10 and these gas components are discharged out successively in that order from the separating column 10. Therefore, when $H_2$ is first discharged out, the gas detector unit 14 indicates an output corresponding to the concentration of $H_2$, and when CO is discharged out next, said detector unit indicates an output corresponding to the CO concentration, and then when $CH_4$ is discharged out, the unit indicates an output corresponding to the $CH_4$ concentration. Thus, by previously determining the calibration curves of the concentrations of the respective gas components in the gas reservoir 4 and the corresponding outputs of the gas detector unit, it is possible to detect the concentration of each gas component.

After completing one cycle of gas detection operation, the four-way change-over valve 7 is again switched to the solid-line position and the air feeder 9 is stopped. Whereupon the gas gain begins to gather in the gas reservoir 4 for the next run of the detection operation.

Driving of the air feeder 9, switching of the four-way change-over valve 7, detection of the gas components, another switching of the four-way change-over valve 7 and stop of the air feeder 9 constitute one cycle of operation, and by repeating this operation periodically, it is possible to monitor the change in the gas components with time. Also, said operation need not be manual but may be automated if so desired.

Figure 2:
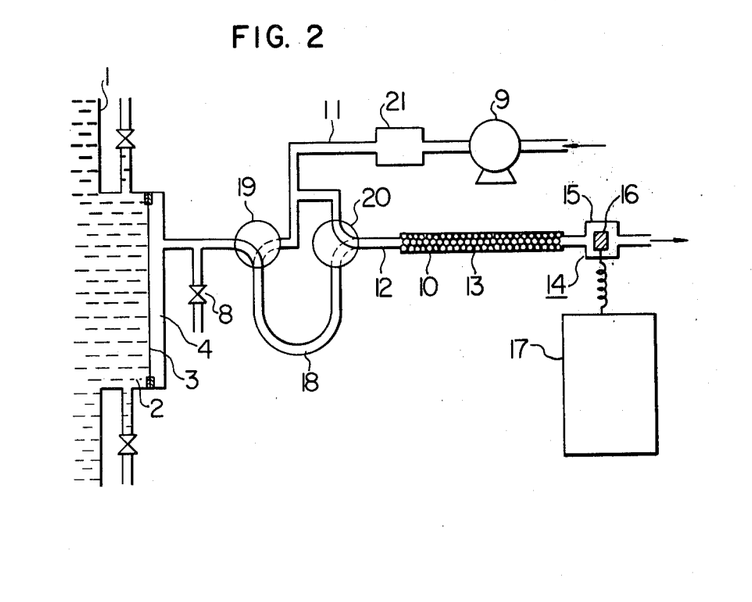

FIG. 2 shows another embodiment of this invention. The differences of this embodiment from the embodiment of FIG. 1 are that a calibration tube 18 of a given capacity is provided in connection to the gas reservoir 4, with three-way change-over valves 19, 20 being provided at both ends of said calibration tube 18, and that a dehumidifier 21 for removing moisture in the air is provided on the outlet side of the air feeder 9.

The gas separating filler 13 is changed in its separating performance and properties as it absorbs moisture, so that by removing moisture in the air with the dehumidifier 21, it is possible to stabilize the properties and to prolong the life of the gas separating filler 13. Said dehumidifier 21 may be provided on the inlet side of the air feeder 9.

In this embodiment, when the gas is collected in the gas reservoir 4, both three-way change-over valves 19 and 20 are set to the solid-line positions so that the gas is collected in the calibration tube 18, too. When performing the gas component detecting operation, said three-way change-over valves 19, 20 are switched to the positions of broken lines in the drawing, allowing the gas in the calibration tube 18 alone to flow into the separating column 10 with the air from the air feeder 9.

This embodiment is otherwise same as that of FIG. 1 in both construction and operation, and hence the like reference numerals are affixed to the like parts and no additional explanation is given to such parts.

This embodiment is particularly useful for the system having a gas reservoir 4 of a large capacity. When the capacity of the gas reservoir 4 is large, the amount of the gas supplied into the separating column 10 increases correspondingly, so that it is difficult with the system of FIG. 1 to separate such large volume of gas into the individual components, but according to the instant embodiment, since the amount of gas supplied into the separating column 10 can be regulated by the capacity of the calibration tube 18, it is possible to distinctly separate the peak values of outputs for the respective gas components.

Also, this embodiment is credited with high safety since the pressure of air supplied from the air feeder 9 does not act on the polymer membrane 3.

Figure 3:
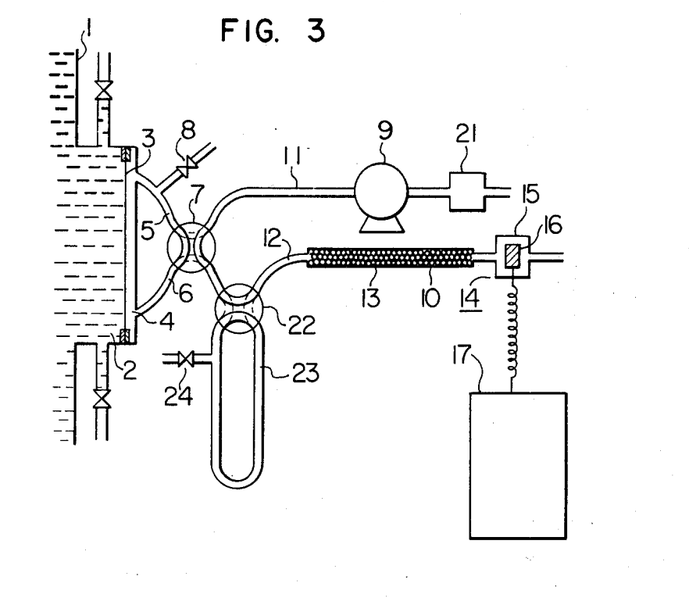

Still another embodiment of this invention is shown in FIG. 3. This embodiment differs from the embodiment of FIG. 1 in that a second four-way change-over valve 22 is provided halfway in the passage 12 connecting the first four-way change-over valve 7 and the separating column 10, with a calibration tube 23 for the reference gas being connected to said second four-way change-over valve 22, and that a dehumidifier 21 is provided on the inlet side of the air feeder 9. Said calibration tube 23 for the reference gas has the same capacity as the gas reservoir 4 and is provided with a valve 24 for controlling feed of reference gas.

The system of this embodiment is operated as follows.

When the gas is pooled in the gas reservoir 4, the two four-way change-over valves 7, 22 are set to the solid-line positions. Before detecting the components of the gas in the gas reservoir 4, the valve 24 is opened to admit the reference gas of a known composition into the calibration tube 23 and then the valve 24 is closed. Then the air feeder 9 is operated to pass air into the separating column 10 and case 15 to adjust the gas detector unit 14. Then the second four-way change-over valve 22 is switched to the broken-line position to let the reference gas in the calibration tube 23 flow into the separating column 10 with the air from the air feeder 9 to perform detection of the gas components. By this operation, it is possible to check whether the relation between the components of the reference gas and the corresponding outputs of the gas detector unit 14 agrees with the already determined calibration curves. If they do not agree, the calibration curves are corrected. Then the second four-way change-over valve 22 is again switched to the solid-line position to pass air into the separating column 10 and case 15, and thereafter the first four-way change-over valve 7 is switched to the dotted-line position. This is followed by the same operation as in the embodiment of FIG. 1 to perform detection of the components of the gas in the gas reservoir 4.

This embodiment is otherwise same as the embodiment of FIG. 1, so that the like reference numerals are affixed to the corresponding parts and no detailed explanation is given to such parts.

According to this embodiment, it is possible to make sure whether the gas separating filler remains unchanged in its properties before detecting the components of the gas in the gas reservoir, and if any change in filler properties is found, one can properly correct the calibration curves or replace the separating column, so that it is possible to perform detection of the components of the gas in the oil in an oil-filled electric device with extremely high accuracy.

The embodiment of FIG. 3 may be practiced in combination with the embodiment of FIG. 2.

Figure 4:
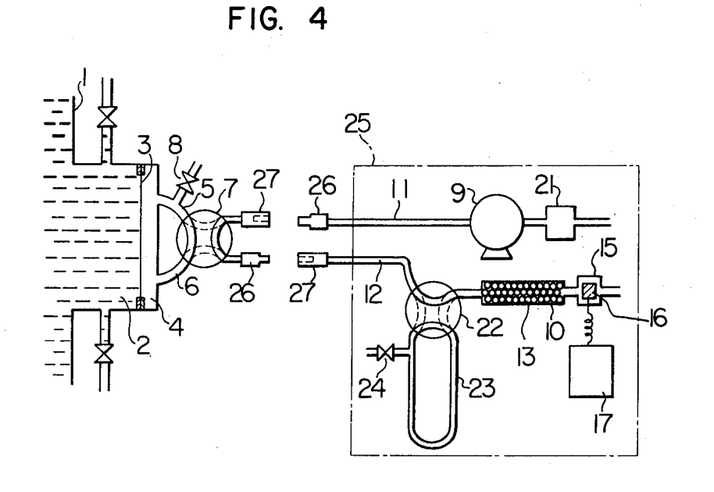

In yet another embodiment of this invention shown in FIG. 4, the parts shown rightwards from the four-way change-over valve 7 in FIG. 3 are assembled as a portable unit 25 indicated by a chain-dot line, and the detachable joint pipes 26 and 27 are provided halfway in the passages 11 and 12, respectively. If the section for separating the gas in the oil and the section for detecting the gas components are constructed so that they are detachable from each other, a single gas component detector unit can be easily adapted to many oil-filled electric devices. The portable construction shown in FIG. 4 can be easily applied to the systems of FIGS. 1 and 2.

The foregoing embodiments of this invention, as described above, are capable of detecting the gas components by separating the gas dissolved in the insulating oil in an oil-filled electric device with no need of sampling out the insulating oil from said device, thereby monitoring the change with time of the gas composition in the insulating oil. Also, since the adjustment of the gas detector unit can be made by passing air through the separating column and the gas detector unit before detecting the gas components in the oil, it is possible to attain accurate detection of the gas components. Further, because of the system in which the gas pooled in the gas reservoir is guided out by air, no much time is required for the detection, and when a sign of abnormality is observed, the detection time interval may be reduced.

As a result of a series of experiments conducted to see the change in the gas dissolved in the insulating oil in case the insulated article in the oil was exposed to discharging and in case said article was heated, the present inventors found the following facts.

Figure 5:
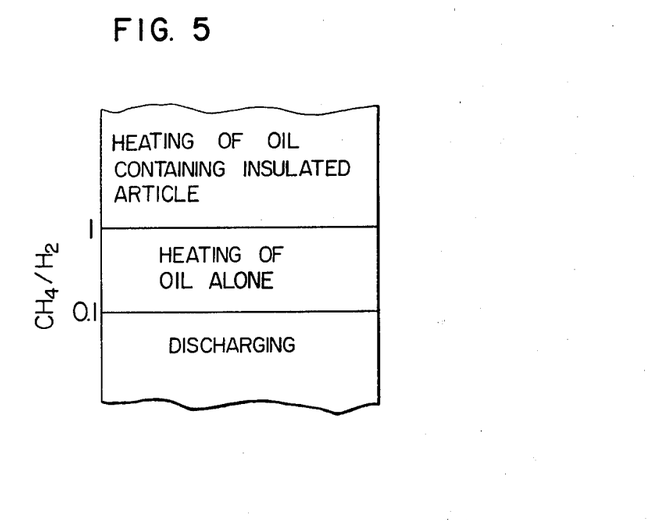
FIG. 5 is an illustration showing the relation between the type of abnormality and $CH_4/H_2$.

(1) There exists a relation such as shown in FIG. 5 between the types of abnormality, that is, discharging, heating of the oil alone and heating of the insulated article in the oil, and the ratio of the components $CH_4$ and $H_2$ ($CH_4/H_2$) in the gas in the oil.

Figure 6:
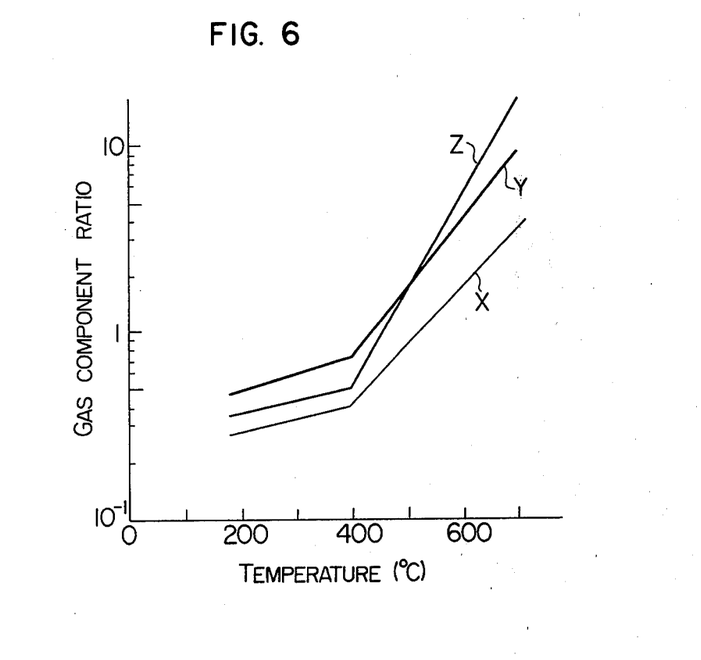
FIG. 6 is a characteristic graph showing the relation between the temperature of heating and the gas component ratio in case oil alone is heated.

(2) In case the oil alone is heated, there exists a relation such as shown by the characteristic lines X ($C_2H_4/C_2H_6$), Y ($C_3H_6/C_3H_8$) and Z ($C_2H_4/C_3H_8$) in FIG. 6 between the temperature of heating and the gas component ratios $C_2H_4/C_2H_6$, $C_3H_6/C_3H_8$ and $C_2H_4/C_3H_8$ in the gas in the oil.

Figure 7:
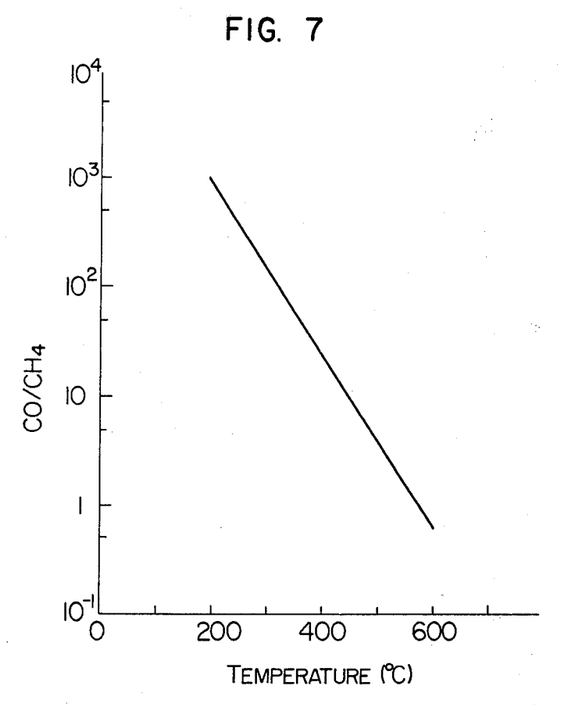
FIGS. 7 and 8 are characteristic graphs showing the relation between the temperature of heating and the gas component ratio in case the insulated article is heated in oil.
Figure 8:
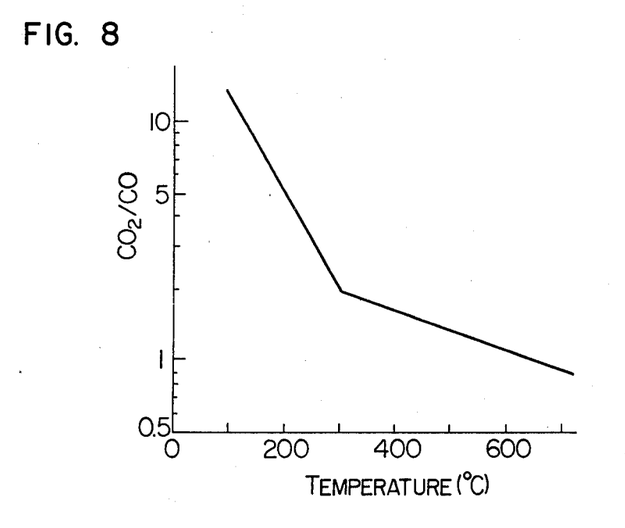

(3) In case the insulated article is heated along with the oil, there exists a relation such as shown in FIGS. 7 and 8 between the temperature of heating and the gas component ratios $CO/CH_4$ and $CO_2/CO$ in the gas in the oil.

If the respective gas component ratios depicted by the graphs can be determined automatically from the above-said relations, then one can readily know the type of abnormality (heating or discharging) in the transformer, and if it is heating, one can know whether it involves the oil alone or further involves the insulated article as well, and also the temperature of heating can be easily known.

Figure 9:
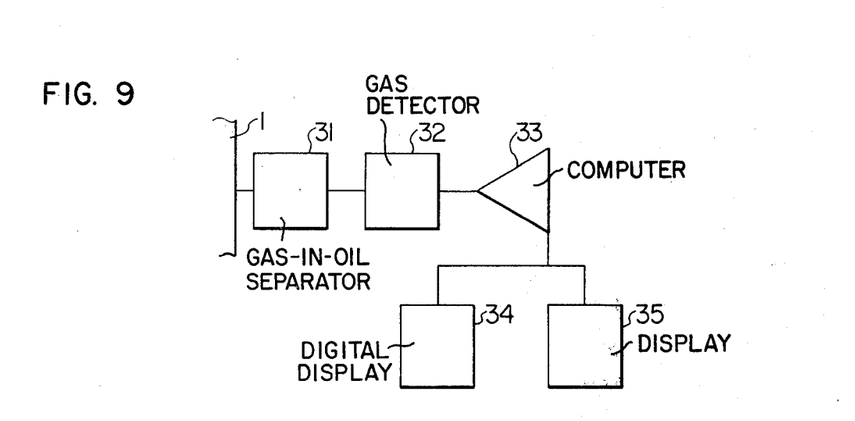
FIGS. 9 to 11 are block diagrams of the system for monitoring an abnormality oil-filled electric devices according to the other embodiments of this invention.

In view of this, the present invention incorporates a gas-in-oil separator 31 utilizing said polymer membrane, Torricelli's vacuum, Toepler pump, piston, etc., in connection to the case 1 of an oil-filled electric apparatus filled with an insulating oil, and the gas separated and extracted in this section is measured by a gas detector unit 32 adopting gas chromatography or various types of sensors, and the data of measurement are sent to a computer 33, as shown in FIG. 9. This computer is so set that it can perform the required calculations, for example, calculations of the amounts of the respective gas components or the gas component ratios such as graphically shown in FIGS. 5 to 8, and the calculated gas components or gas component ratios are each displayed with a figure by digital display device 34. Also, the type of abnormality determined from the result of calculations by said computer 33 is indicated on another display device 35. The display device 35 indicates the presence or absence of abnormality and the type of abnormality (for example, heating or discharging) in case abnormality is present. It also indicates, in case the abnormality is heating, whether the oil alone is involved or the insulated article is also heated with the oil, while showing the temperature of heating as well.

Said series of units 31-35 are automated, allowing automatic measurement and indication of the presence or absence of abnormality in the case 1 of an oil-filled electric device, the type of abnormality in the event of presence of abnormality (by utilizing the characteristics depicted in FIGS. 5 to 8) and even the temperature of heating in case the abnormality is heating.

A practical mode of gas detection by the system of this invention for an oil-filled electric device is described below.

In this embodiment, a gas-in-oil extractor utilizing Torricelli's vacuum is used as the gas-in-oil separator 31 and gas chromatography is employed for the gas detector unit 32. The computer 33 which calculates the data from the gas chromatography is so set that it can calculate the amounts of the respective components in a combustible mixed gas as well as the values of $CH_4/H_2$, $C_2H_4/C_2H_6$ and $CO_2/CO$. The system is also provided with a display device 34 for indicating the amounts of the gas components and the gas component ratios and another display device 35 for indicating the type of abnormality. Said display device 35 gives an indication of abnormality when the total amount of the combustible gas reaches 1,500 ppm or above and also gives an indication of "discharging" when $CH_4/H_2 < 0.1$, "heating of oil alone" when $0.1 \leq CH_4/H_2 \leq 1$ and "heating of insulated article" when $CH_4/H_2 > 1$. Also, in case the abnormality is heating of oil alone, the temperature is indicated by the value of $C_2H_4/C_2H_6$ and in case the abnormality is heating of insulated article, the temperature is indicated by the value of $CO_2/CO$.

EXAMPLES 1-4

In case the amounts of the respective gas components determined by the gas chromatography are of the values shown in Table 1, the amount of the combustible gas and the gas component ratios to be indicated by the display device 34 are calculated by the computer 33 and given as shown in Table 2. As a result, the abnormality type display device 35 indicates "abnormality, heating of oil alone to approximately 460° C." in the case of Example 1, "abnormality, heating of insulated article to approximately 300° C." in the case of Example 2, "abnormality, discharging" in the case of Example 3, and "no abnormality" in the case of Example 4.

TABLE 1

| | Gas components | | | | | | Unit: ppm Total amount of combustible gas |
|---|---|---|---|---|---|---|---|
| Example | $H_2$ | CO | $CO_2$ | $CH_4$ | $C_2H_4$ | $C_2H_6$ | |
| 1 | 400 | 130 | 1000 | 300 | 355 | 350 | 1535 |
| 2 | 300 | 1000 | 2000 | 500 | 240 | 350 | 2390 |
| 3 | 1300 | 20 | 500 | 90 | 75 | 70 | 1555 |
| 4 | 1000 | 10 | 500 | 80 | 90 | 70 | 350 |

TABLE 2

| | Gas component ratio | | |
|---|---|---|---|
| Example | $CH_4/H_2$ | $C_2H_4/C_2H_6$ | $CO_2/CO$ |
| 1 | 0.75 | 1.01 | 7.69 |
| 2 | 1.7 | 0.69 | 2.00 |
| 3 | 0.07 | 1.07 | 25 |
| 4 | — | — | — |

In the foregoing embodiments, a device applying Torricelli's vacuum is used as the gas-in-oil separator 31 and gas chromatography is employed for the gas detector unit 32, so that the system is rather complicated and costly. Therefore, use of the following system is suggested as a more simple and uncostly system.

Figure 10:
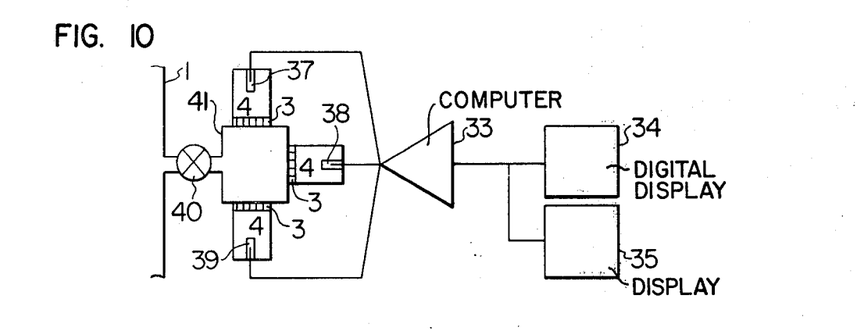
Figure 11:
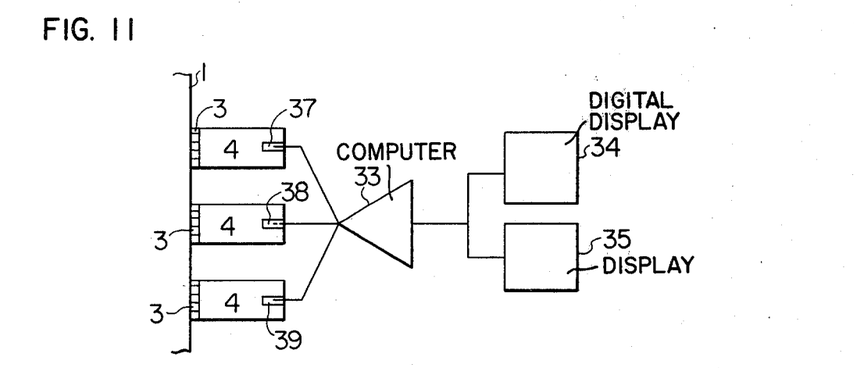

Described here is an example where the gas components are separated from the oil by using a polymer membrane, such as employed in the examples of FIGS. 1 to 4, for the gas-in-oil separator 31. In this case, among the gas components that can be extracted from the oil by the polymer membrane, usually $H_2$ is predominent, and CO and $CH_4$ come next. So, we describe hereinbelow an example where the abnormality in an oil-filled electric device is monitored by detecting said gas components which permeate said polymer membrane at relatively high rates. Since the principal components of the gas that permeates the polymeric membrane are $H_2$, CO and $CH_4$, there are adapted a $H_2$ gas sensor 37, a CO gas sensor 38 and a $CH_4$ gas sensor 39 in the gas detector unit as shown in FIGS. 10 and 11. These sensors 37–39 are disposed in the respective gas reservoirs 4 designed to collect the gas which has passed through the respective polymer membranes 3 from a single adaptor 41 connected to the case 1 of an oil-filled electric device through a flanged valve 40 as shown in FIG. 10. The gas reservoirs 4 may be provided separately for the respective gas components $H_2$, CO and $CH_4$ in direct attachment to the case 1 through the respective polymer membranes 3 as shown in FIG. 11, or all of the three sensors may be disposed in a single gas reservoir. The values of $H_2$, $CH_4/H_2$ and $CO/CH_4$ are automatically calculated by the computer 33 according to the inputs sent from the respective gas sensors 37–39, and the calculated values of $H_2$, $CH_4/H_2$ and $CO/CH_4$ are indicated on the display 34. Here, presence or absence of abnormality is judged according to the value of $H_2$ while the type of abnormality is judged according to the value of $CH_4/H_2$. In the case of heating of the insulated article, its temperature is determined according to the value of $CO/CH_4$.

These setting values may be selected optionally, but in the instant examples of this invention, the amount of $H_2$ of 400 ppm or above was set as an indication of abnormality. Also, according to the relations shown in FIG. 5, the abnormality is judged as "charging" when $CH_4/H_2 < 0.1$, "heating of oil alone" when $0.1 \leq CH_4/H_2 \leq 1$, and "heating of insulated article" when $CH_4/H_2 > 1$.

Examples 5–8

In case the gas components detected by the gas detector unit are of the values shown in Table 3, the values of $CH_4/H_2$ and $CO/CH_4$ indicated by the display 34 are as shown in Table 4. Consequently, the abnormality type display 35 indicates "abnormality, heating of oil alone" in the case of Example 5, "abnormality, heating of insulated article to 500° C." in the case of Example 6, "abnormality, discharging" in the case of Example 7, and "no abnormality" in the case of Example 8.

TABLE 3

| Example | Gas components | | | Unit: ppm Total amount of combustible gas |
|---|---|---|---|---|
| | $H_2$ | $CH_4$ | CO | |
| 5 | 500 | 240 | 60 | 800 |
| 6 | 450 | 800 | 1300 | 3550 |
| 7 | 1400 | 50 | 50 | 1490 |
| 8 | 100 | 30 | 50 | 180 |

TABLE 4

| Example | Gas component ratio | |
|---|---|---|
| | $CH_4/H_2$ | $CO/CH_4$ |
| 5 | 0.48 | 0.25 |
| 6 | 1.80 | 2.88 |
| 7 | 0.036 | 0.8 |
| 8 | — | — |

As described above, according to the system of this invention, the amounts of at least the components $CH_4$ and $H_2$ in the gas separated from the insulating oil in an oil-filled electric device are measured separately and the type of abnormality is judged from the gas component ratios calculated therefrom. Thus, the present system is capable of not only detecting the presence of abnormality but also automatically indicating whether such abnormality is discharging or heating of the oil alone or heating of the oil including the insulated article.

What is claimed is:

1. A system for monitoring an abnormality of oil-filled electric devices comprising a gas-in-oil separator which separates the gas staying dissolved in the insulating oil in the casing of an oil-filled electric device, a gas reservoir where the separated gas is collected, an air feeder which supplies air for delivering out the gas in said gas reservoir, a separating column packed with a gas separating filler whereby the gas supplied thereinto from said gas reservoir is separated into the respective components, a gas detector unit comprising a combustible gas detector element, made from a semiconductor element which varies in its internal impedance when contacted with a combustible gas, disposed in a case which connects at its one end to the outlet of said separating column and opens at its other end into the atmosphere, and a change-over valve disposed at a location connecting said gas reservoir, said air feeder and said separating column and adapted to switch a route which passes air from said air feeder along with said gas into said separating column via said gas reservoir to and from a route which passes said air directly into said separating column.

2. A system according to claim 1, wherein said gas reservoir is provided with a calibration tube and the gas in said calibration tube is guided into said separating column by the air from said air feeder.

3. A system according to claim 1 or 2, wherein a calibration tube for a reference gas is provided through a change-over valve halfway in the route which passes air from said air feeder directly into said separating column.

4. A system according to claim 1 or 2, wherein a dehumidifier is provided on the inlet or outlet side of said air feeder.

5. A system for monitoring an abnormality of oil-filled electric devices comprising a gas-in-oil separator which separates the gas staying dissolved in the insulating oil in the casing of an oil-filled electric device, means for detecting the components in the separated gas, means for separately measuring the amounts of at least the components $CH_4$ and $H_2$ in the separated gas, and means for determining the ratio of the measured amounts of the components $CH_4$ and $H_2$, whereby in case it is judged that abnormality is present, such abnormality is judged as occurrence of discharging when said ratio is below a first setting value, occurrence of heating of the insulating oil alone when said ratio is above said first setting value but below a second setting value, and occurrence of heating of the insulating oil including the insulated article when said ratio is above said second setting value.

6. A system according to claim 5, further comprising means for measuring the amount of CO in the separated gas and means for determining a ratio of CO to $CH_4$, whereby when heating of the insulating oil including the solid insulated article is judged as occurring, the temperature of such heating is determined from said ratio.

7. A system according to claim 5, further comprising means for separately measuring the amounts of $CO_2$ and CO in the separated gas and means for determining a ratio of $CO_2$ to CO, whereby when heating of the insulating oil including the solid insulated article is judged as occurring, the temperature of such heating is determined from said ratio.

8. A system according to claim 5, further comprising means for separately measuring the amounts of $C_2H_4$ and $C_2H_6$ in the separated gas and means for determining a ratio of $C_2H_4$ to $C_2H_6$, whereby when heating of the insulating oil alone is judged as occurring, the temperature of such heating is determined from said ratio.

9. A system according to claim 5, further comprising means for separately measuring the amouns of $C_3H_6$ and $C_3H_8$ in the separated gas and means for determining a ratio of $C_3H_6$ to $C_3H_8$, whereby when heating of the insulating oil alone is judged as occurring, the temperature of such heating is determined from said ratio.

10. A system according to claim 1, further comprising means for separately measuring the amounts of $C_2H_4$ and $C_3H_8$ in the separated gas and means for determining a ratio of $C_2H_4$ to $C_3H_8$, whereby when heating of the insulating oil alone is judged as occurring, the temperature of such heating is determined from said ratio.

11. A system according to claim 5, further comprising means for indicating the results of judgement of occurrence of discharging, occurrence of heating of the insulating oil alone, and occurrence of heating of the insulating oil including the solid insulated article.

12. A system according to claim 5, wherein the means for detecting the components includes a combustible gas detector element made from a semiconductor element which varies in its internal impedance when contacted with a combustible gas.

* * * * *